United States Patent [19]

Brossia et al.

[11] Patent Number: 4,851,817
[45] Date of Patent: Jul. 25, 1989

[54] FIBER OPTIC PROBE SYSTEM

[76] Inventors: Charles E. Brossia, 7997 S. Pontiac Way, Englewood, Colo. 80112; Samuel C. Wu, 10205 W. Exposition Ave., Lakewood, Colo. 80226

[21] Appl. No.: 838,283

[22] Filed: Mar. 10, 1986

[51] Int. Cl.⁴ ............ G08B 19/02; G08B 17/12; G01W 1/00

[52] U.S. Cl. ............ 340/583; 340/600; 340/601

[58] Field of Search ............ 340/580–583, 340/555–557, 600–601, 619; 73/170 R, 171, 293; 250/227, 577, 574, 573; 356/73.1; 137/558, 392; 350/96.23, 96.29–96.34

[56] References Cited

U.S. PATENT DOCUMENTS

| | | | |
|---|---|---|---|
| 3,045,223 | 7/1962 | Kapany et al. | 340/583 |
| 3,540,025 | 11/1970 | Levin et al. | 340/583 |
| 4,159,420 | 6/1979 | Tsunoda | 340/619 X |
| 4,335,613 | 6/1982 | Luukkala | 340/582 X |
| 4,379,289 | 4/1983 | Peek | 340/600 X |
| 4,468,567 | 8/1984 | Sasano et al. | 340/619 X |

Primary Examiner—Glen R. Swann, III
Assistant Examiner—Thomas J. Mullen, Jr.
Attorney, Agent, or Firm—Klaas & Law

[57] ABSTRACT

A system for automatic and real time detection of water and icing on surfaces by monitoring variations in light energy transmitted through an optical fiber having a specially processed sensitive area probe. The sensitive probe area is positioned on, about or within the surface on which icing is to be detected. Because of differences in optical indices of refraction and energy absorption characteristics of air, water and ice, the presence of each of these at the processed sensitive area will cause a proportional and characteristic attenuation of the light energy passing through the optical fiber. Changes in light energy transmission can be interpreted automatically to provide an indication of icing. A reference optical circuit may be used to provide compensation for variations in input energy levels. Light energy of different wave lengths and energy levels may be used to compensate for or avoid interference with measurement by ambient lighting conditions or for the detection of other conditions and materials using the principle of characteristic absorption and resonance.

30 Claims, 4 Drawing Sheets

FIBER OPTIC PROBE SYSTEM

FIELD OF THE INVENTION

This invention relates generally to apparatus and methods for detecting the presence of a substance such as water and/or a change in condition of a substance such as change from water to ice by use of light. More particularly, the present invention relates to an apparatus and method for the detection of the presence of ice and the ice accretion rate at a preselected location such as aircraft airfoil surfaces, aircraft engine intake surfaces, street highway surfaces and airport runway surfaces, automobile undercarriage surfaces and home appliances.

BACKGROUND AND SUMMARY OF INVENTION

Numerous attempts have been made over a period of more than forty years to develop ice detection systems as illustrated by Hall U.S. Pat. No. 2,269,019; Peters, et al. No. 2,359,737; Thoma No. 4,327,286; Forgue No. 4,333,004; Kovaca No. 4,379,227; Chamuel No. 4,461,178 and Magenheim et al., No. 4,470,123, the disclosures of which are incorporated herein by reference.

In recent years efforts have been made to develop fiber optic technology for various purposes including the use of a bent fiber optic refractometer device for measurement of salinity in double diffusive thermohaline systems as described in Rev. Sci. Instrum. 56(2), Feb. 1985 of the American Institute of Physics, the disclosure of which is incorporated herein by reference. Powell U.S. Pat. No. 4,256,403, the disclosure of which is incorporated herein by reference, discloses a water contaminate and fuel density detector using a longitudinally extending body of light transmitting material with light emitting means at one end to provide a group of divergent rays in angularly disposed light emission paths onto a plurality of vertically spaced light sensors for producing a signal corresponding to the index of refraction indicating the density of the fuel, while also indicating the presence of water in the fuel.

In general, the present invention utilizes a sheathed and/or coated optical fiber means having a first sheathed and/or coated light path portion connected to a light emitting device for transmitting light from the light emitting device along a first covered light transmission path, an intermediate, unsheathed, exposed core portion having an abraded peripheral surface for providing a sensor means, and a second sheathed and/or coated path portion connected to a light receiving device for receiving transmitted light from the light source and generating variable output signals dependent on characteristics of received light. The optical fiber device is constructed and arranged to prevent light loss in the first path portion and the second path portion with variable light losses occurring in the intermediate portion depending upon variations in environmental conditions at the intermediate portion. The variable light losses in the intermediate portion are dependent on the reflection and refraction characteristics of the intermediate portion of the optical fiber device and the reflection and refraction and absorption characteristics of the environmental medium in contact with the intermediate portion. Since various characteristics, such as reflection, refraction, heat of fusion, rate of temperature change in various phases, etc., of various mediums, such as air, water, ice, corn oil, gasoline, etc., are known or can be determined, the amount of light loss in the intermediate portion can be calculated with respect to various surrounding mediums. Differences in the amount of light received by the light measuring device can be used to indicate the nature or phase (i.e., solid, liquid, gaseous) of the environmental medium in contact with an outer surface of the intermediate portion of the optical fiber device.

The present invention provides an apparatus and methods for detecting the buildup of ice on surfaces, which apparatus and methods are capable of distinguishing between water and ice on the surface being observed, and for other purposes such as detecting the presence of water in gasoline or oil or level of liquids in a vessel. The detection of the buildup of ice on surfaces is provided by measurement of the difference between the light energy absorption and refractive indices of dissimilar materials using a sensor probe of special design. The system of the present invention provides for automatic and real time detection of water and icing on surfaces by monitoring variations in light energy transmitted through a bent optical fiber having a specially processed sensitive area at its bend. The sensitive area is preferably positioned adjacent, on, about or within the surface on which icing is to be detected. Because of differences in the optical indices of refraction and energy absorption characteristics of air, water and ice, the presence of one of these mediums on the surface of the optical fiber core at the processed sensitive area, will cause a proportional and characteristic attenuation of the light energy passing through the optical fiber. The resultant observed changes in light energy transmission can be interpreted mathematically to produce an indication of the presence of ice or other material on the surface being tested. A reference optical circuit may be used to provide compensation for variations in input energy levels, temperature, physical stress, ambient light, etc. Light energy of different wave lengths and energy levels may be used to compensate for or avoid interference with measurement that could be produced by differences in ambient lighting conditions or for the detection of other conditions and materials using the principle of characteristic absorption and resonance. The rate of ice accretion or precipitation may also be measured by the use of a capacitance system or an electrically conductive heater wire positioned on or about the sensitized area of the optical fiber.

BRIEF DESCRIPTION OF THE DRAWINGS

Illustrative and preferred embodiments of the invention are shown in the accompanying drawings wherein.

DETAILED DESCRIPTION

Figure 1:
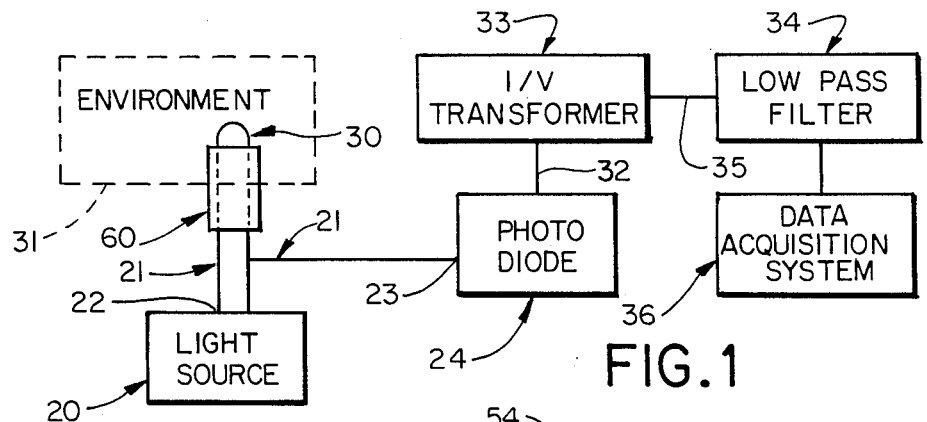
FIG. 1 is a schematic block diagram of a condition detection system of the present invention.
Figure 2:
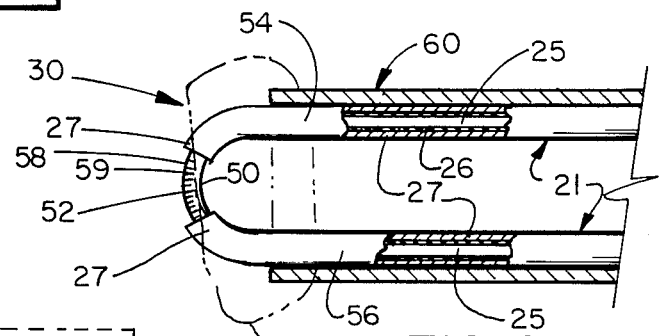
FIG. 2 is a partial cross-sectional view of a sensor element according to the present invention.

In general, as shown in FIGS. 1 & 2, the present invention employs a light source means 20, such as a conventional infrared light emitter device (LED) for continuously or intermittently generating light when connected to a power supply. A fiber optical cable means 21 is connected at one end portion 22 to the light source means 20 for continuously transmitting light beams along the fiber optical cable means to an end portion 23 connected to conventional light receiving and signal generating detector means 24, such as conventional infrared light receiving device (LRD), for generating variable output signals which vary in accordance with the amount of light transmitted thereto. The fiber optical cable means 21 is of conventional design, except as modified as hereinafter described, and comprises one or more core fibers 25 having a generally cylindrical outer peripheral surface configuration. The entire outer surface of the core fiber or fibers is conventionally covered by an optical coating or cladding material 26 which prevents lateral transmission of light while enabling only longitudinal transmission of light. A protective sheath 27 is usually provided circumjacent the coated core fiber or fibers. A condition sensing probe means 30 is operably associated with the fiber optical cable means to provide a section in the light transmission path wherein the amount and intensity of light travelling through the fiber optical cable means 21 to the associated detector means 24 is varied in accordance with a change in condition of a sensed medium in an environment 31 associated with the condition sensing probe mean 30 whereby an output signal from detector means 24 on an output line 32 is varied in accordance with a change in condition of the sensed medium. The detector output signal may be transmitted to a conventional I/V transformer means 33 which transmits a corresponding signal to a conventional low pass filter means 34 through a line 35 and then to a conventional data acquisition system means 36 whereat changes in the output signal are utilized to determine changes in and state of condition of the medium.

Figure 3:
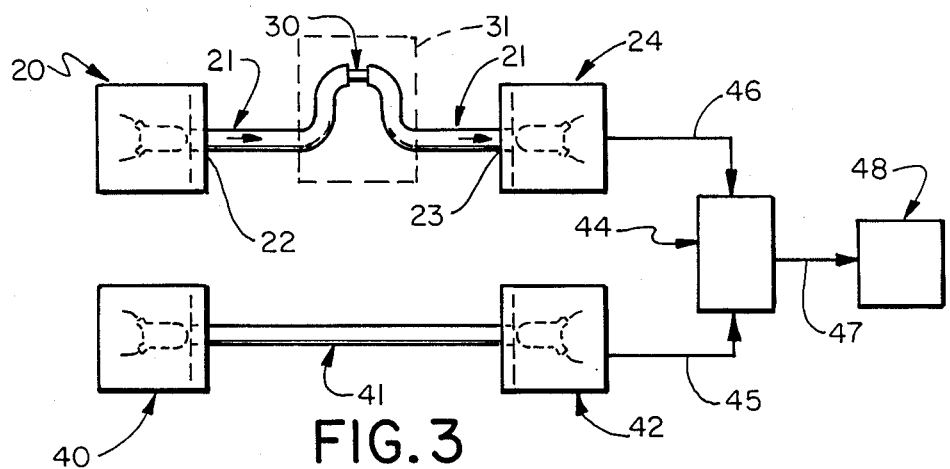
FIG. 3 is a schematic block diagram of a presently preferred embodiment of a condition detection system of the present invention.

In a presently preferred embodiment, as shown in FIG. 3, a reference signal generating means is employed which comprises a light source means 40, a fiber optical cable means 41, and a light receiving and signal generating detector means 42, all of the same type as previously described, but which may or may not include a sensor probe means 30 or other reference condition indicating means. A reference output signal generated by reference signal light detector means 42 and the condition signal generated by condition sensing detector means 24 are transmitted to a conventional electronic controller means 44 via lines 45, 46 for comparison of the signals and for generation of a control signal on line 47 representative of the change in condition at sensor means 34. The control signal is transmitted to a conventional control output means 48 such as an Apple-type personal computer for providing a visual or audible indication of the change in or condition of the medium.

In the presently preferred embodiment, the sensor probe means 30 comprises a portion of the fiber optical cable means 21 from which the sheathing material 27 and the coating material have been removed to provide an exposed medium contact area in which the core fiber or fibers have no sheathing nor coating precluding transfer of a portion of the light therethrough. The exposed medium contact area is preferably formed at an U-shaped loop section 50, as shown in FIG. 2, of the fiber optical cable means which has a curved portion 52 and parallel side portions 54, 56. An outermost surface 58 on curved portion 52 is provided with transverse striations 59 thereacross which may be formed during removal of the coating material by lightly sanding the peripheral surface of the core fiber or fibers with abrading material such as a piece of sandpaper, preferably 600 grit silicon carbide, or the like. The U-shaped loop section 50 may be mounted in a support means, such as a cylindrical tubular member 60, with a protecting, sealing and retention means, such as an adhesive sealing material 62, associated therewith. Support means 60 is mounted in a suitable manner on or in support structure, such as an airplane, runway, engine, refrigerator, etc., so as to locate the sensing area in the environment where the change of condition is to be sensed.

Figure 9:
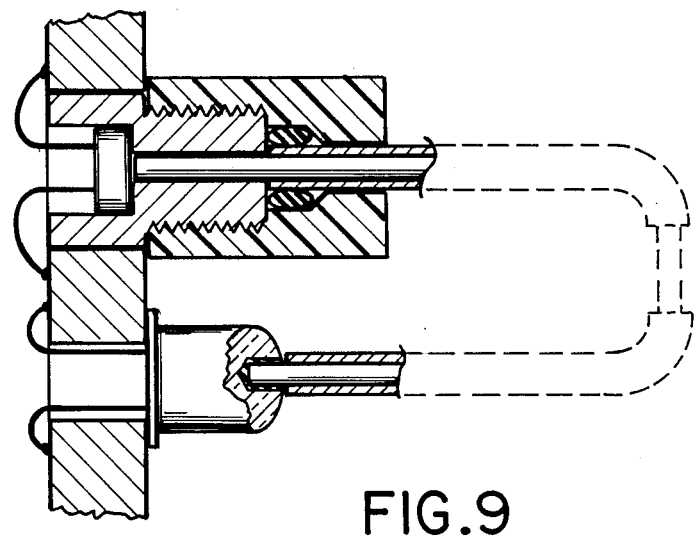
FIG. 9 is a partial cross-sectional view of a probe assembly.

FIG. 9 shows an assembly wherein the emitter means 20 and the detector means 24 are mounted on a printed circuit board 70 with leads 72, 74 connected thereto in a conventional manner. End portion 22 of optical fiber means 22 is connected to emitter means 20 by drilling a hole 76 in the end of the emitter means to receive core end portion 78 which is secured therein by a conventional optical grade adhesive material 80. If a reference optical fiber means 41 is used, it may be connected to the same emitter means 20 by drilling a second hole parallel to hole 76 and connected to a second detector means 42 mounted adjacent detector means 24. Optical fiber end portion 23 is connected to detector means 24 by a conventional coupling means 82 comprising a threaded plug member 84 having a central bore 86 to receive and hold unsheathed core end portion 88 in face to face contact with the detector plate 90. A threaded cap member 92 has a central bore 94 to receive sheathed optical fiber portion 95 and a compressible retaining ring means 96.

The fiber optical cable means is preferably a conventional PVC sheathed fiber optical light transmitting device made of polystyrene or acrylic or polymethyl methacrylate polymer fiber core section having a diameter of one millimeter such as Model No. P1000 of General Fiber Optics Co. A sensor area is made by removing approximately two and ½ inches of the sheathing and also removing approximately ⅝ to 11/16 of the cladding and/or coating material centrally of the non-sheathed area. The entire circumference of the outer surface of the exposed section of the polymer fiber core is abraded by lightly sanding with a piece of 600 grit silicon carbide sandpaper by movement of the sandpaper around the peripheral surface transversely to the longitudinal axis of the polymer fiber to produce a roughened surface with circumferentially extending striations along the exposed section of the polymer fiber core to produce a cylindrical surface sensor area therealong. Good results are obtained when the sanded area produces between approximately 50 to 70 percent light attenuation in air and approximately 60 percent attenuation is preferred. It has been discovered that unsatisfactory results are obtained without sanding the exposed section and also, if the sanding occurs parallel to the central longitudinal axis, rather than laterally thereof. Then, the fiber optic device may be bent at the sensor area to provide a loop having a radius of approximately 9/16 inch to provide an U-shaped probe portion. However, it has been discovered that the sensor area will operate satisfactorily in a straight line condition or a partially curved condition. A conventional 100 mA P-N gallium aluminum arsenide 880 nanometer infrared light emitting device, TIL906-1 available from Radio Shack, or MFOE71 manufactured by Motorola Corporation, and a conventional photo darlington-type light activated receiving and signal generating device, MFOD73, manufactured by Motorola Corporation, are fixedly sealably associated with and connected to opposite end portions of the fiber optic device in closed light transmitting and receiving relationship therewith.

Tests have shown that the characteristics of the sensor surface and the light emitting device are very important to successful operation. The sensor surface irregularities provide an opportunity for light to refract or bend out of the fiber and into the sensed medium. The more irregularities there are, the more opportunities there are for energy passing through the fiber to interact with the sensed medium. The energy that has been refracted into the sensed medium has an opportunity depending upon the geometry of the scratch to either refract back into the fiber, be absorbed by the sensed medium or pass on into the ambient where it is eventually absorbed.

The attenuation of light propagating through a treated optical fiber has been investigated and repeatable experiments have demonstrated that the light passing through the fiber is increasingly attenuated when air, ice and liquid water, respectively, are present on the treated portion of the fiber probe.

Initial experiments indicated that treating the fiber probe in accordance with the present invention significantly enhanced the observed phenomenon. The treatment consisted of cross sanding the fiber, in a direction perpendicular to the fiber axis, with a fine grit #600 sandpaper.

The results of experiments indicate a linear increase in the attenuation of the light passing through a treated portion of a fiber depending upon the amount of abrasion. For example, a single abrasion stroke caused attenuation approximately 50 times greater than before treatment and four strokes caused attenuation approximately 250 times greater than before treatment. The result suggests there is a strong correlation between the rate of change in the attenuation of the light passing through the fiber and the degree of surface abrasion and number of the grooves as well as the total abraded area. Other experimental results provide evidence on the effect of the nature of the surface grooves in the observed phenomenon. Fibers that were treated by sanding parallel to the axis of the fiber showed a less-pronounced effect.

An experimental model was developed as the result of electron micrograph studies. Electron micrographs of the treated fibers indicate the surface morphology of the fiber can be approximated by a geometry similar to that diagrammed in FIG. 10. Since the geometry appears to be somewhat similar to a thread configuration, we contemplate that a thread cutting or an ion beam milling technique may be employed to cheaply, reliably and reproducibly provide the required sensor surface configuration.

Figure 10:
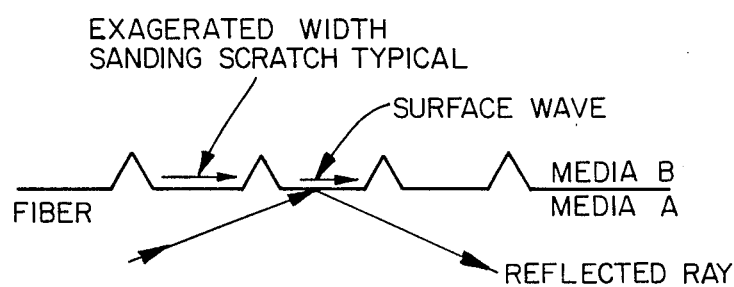
FIG. 10 is a schematic representation of a probe surface.

Most of the light propagating through the fiber is totally internally reflected off the inner surface of the fiber. The phenomenon of total internal reflection was observed centuries ago and is adequately described within the framework of classical electromagnetic theory. When light is totally internally reflected off a boundary separating medias A and B, there exists a surface electromagnetic wave that propagates parallel to boundary (FIG. 10). The electromagnetic fields of the wave, the evanescent fields, are attenuated at an exponential rate into media B.

The surface wave, produced by total internal reflection, will be located within approximately one-half micron or less, from the outer surface of the fiber at the bottom of the groove so as to fully interact with the surface incongruities of the treated fiber. Electron micrographs of the treated fibers indicate the surface irregularities are on the order of ten microns or more in height and substantially greater than the location of the surface wave. Thus, the evanescent fields of the electromagnetic surface wave go to zero well under the height of the surface incongruities and the surface wave strongly interacts with the surface morphology created by the fiber treatment.

When a surface wave encounters an obstruction, a portion of the wave is transmitted back into the fiber. A mathematical model of the interaction of the evanescent fields and the surface topography of a treated fiber has been constructed. The model assumed liquid water, ice or air on the fiber surface and computed the relative intensity of the light transmitted through the fiber. The results predict the light propagating through the fiber should be attenuated most when air is in contact with the fiber surface, a bit less for ice and least for liquid water. The results are in accordance with all the observed experimental results described previously.

An investigation of the physical principles involved to understand the observed phenomenon has been conducted. A number of experiments indicate the sanding treatment of the optical fiber significantly enhances the observed effect. A mathematical model has been constructed that assumes the basis for the effect is the interaction of the evanescent fields of a surface electromagnetic wave with the irregular surface topography of the treated fiber. The model predicts results that are in accordance with the observed experimental results. Thus, mathematical models may be developed for various environments, mediums and apparatus which would treat the fiber as an electromagnetic wave-guide with an accurate numerical description of the surface irregularities.

Since light that is refracted back into the fiber is sensed by the photodetector attached to the end of the fiber light path, absorption characteristics are important. In testing for water and ice, the sensing fiber has been found to be most sensitive when the energy input is above nominally 500 nanometers wavelength. Tests have shown that emitters with nominal output of 880 nanometers produce good results. The wavelength is outside the visible spectrum in what is referred to as near infrared. We believe that longer wavelength emitter and detector pairs would be more sensitive.

The reason for the increased sensitivity when using the longer wavelength emitters is related to the absorption characteristics of water. The relationship between absorption characteristics and wavelength for water are known. One of the conclusions that may be drawn from this information is that 880 nm wavelength energy is absorbed at rate approximately 6000 times greater than 490 nm wavelength energy. This absorption characteristic is true for liquid water as well as ice and humid air. We have demonstrated in our experimentation the ability to reliably sense the relative humidity of an air sample with exactly the same apparatus used to detect the presence of ice and water.

Our conclusion is that sensitivity to a given medium can be enhanced by selection of an emitter having an output wavelength that is strongly absorbed by the sensed medium. In one experiment, we used a fiber sensor using a dual wavelength output emitter (565 nm and 695 nm). It is conceivable that the concept of multiple as above or continuously variable wavelengths (using a tuneable laser for example) could be used to construct a multiple media sensing device for the detection of media having discrete multiple absorption wavelength bands.

In operation, the LED and the LRD are connected to suitable low DC voltage (e.g., 1.5 volt) power supply circuits which may be battery operated. The LRD output circuit is connected through suitable intermediate circuitry to data acquisition means such as an IBM PC-XT computer with ASYST programming and a Keithly Series 500 system for data acquisition and plotting. Measurements are then made under normal operating conditions with the sensor area exposed to air to establish normal standard voltage output of the LRD (e.g., 1.5 to 2 volts) in an air environment. Then, the probe area is subjected to a water environment so that the exterior surface of the probe area is in intimate surface contact with water. Measurements are then made to establish a normal standard voltage output of the LRD in a water environment which will be substantially different (e.g., a thirty percent shift) than the normal standard voltage output of the LRD for an air environment Measurements are then made to establish a normal standard voltage output of the LRD in an ice environment which will also be significantly and measurably different (e.g., a downward five to fifteen percent shift) from the voltage output of the LRD for the water environment. These measurements may be utilized to establish reliable air-water-ice indicator signal calibration standards to cause visual and/or audible indications of conditions at the sensor area. In order to provide more reliability at lower cost, a reference signal system comprising a fiber optic cable device and associated LED and LRD and circuitry is employed as shown in FIG. 3. The reference signal fiber optic cable device is identical in construction, size, arrangement and location to the condition sensing cable device except that the reference signal fiber optic cable device may or may not have a sensor area or other reference condition indicating means. Thus, the reference signal system is subject to substantially the same environmental and operating conditions as the condition sensing system whereby the effect of ambient light, length, curves, bends, temperature, humidity, etc. variations can be taken into account in processing the condition sensing output signal to establish the presence of water or ice at the sensing area. Preferably, a single light source is used so that both cable devices receive light from the same source.

In operation of the system of FIG. 3, light signals are received by photodetectors 24 and 42 through fibers 21 and 41, respectively. Signal strengths detected by the detectors are compared in a controller circuit 44. The strength of the signals is monitored for changes which indicate there is water or ice at the sensing site. Tests have shown that a thirty percent signal strength shift indicates there is water at the sensing section 30 of fiber 21 and a subsequent signal strength shift further indicates that water is freezing on the sensing section. These signal shifts may be used to cause the output device 48 to be activated in an appropriate manner such as providing a warning light or alarm.

Figure 4:
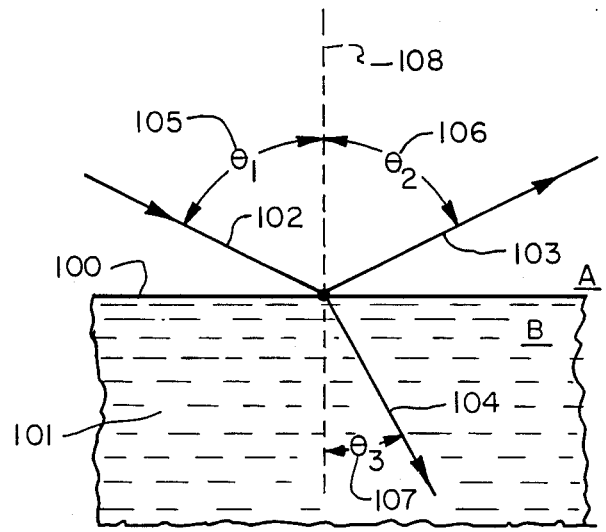
FIG. 4 is a diagrammatic illustration of the optical properties of light incident upon a transparent or translucent layer.

The aforedescribed apparatus and methods for detecting changes in conditions of a medium are based in part upon the use of the differences between refractive indices of different materials. Index of refraction of different materials is a measure of the ratio of the phase velocity of light in a vacuum to that in the predetermined material. FIG. 4 diagrammatically illustrates that a light beam falling upon a transparent or translucent medium surface 100 is both reflected from the surface and bent or refracted as it enters the medium 101. The incident light beam is represented in FIG. 1 by a single line, the incident ray 102, parallel to the direction of propagation. The reflected and refracted beams are also represented by rays 103 and 104, respectively. The angle of incidence 105, angle of reflection 106, and angle of refraction 107 are measured between the normal to the surface 108 and the appropriate ray as shown in the figure. The physical laws governing reflection and refraction are as follows:

$$\text{For reflection: } \theta_1 = \theta_2$$

$$\text{For refraction: } \frac{\sin\theta_1}{\sin\theta_3} = n_{21}$$

where $n_{21}$ is a constant called the index of refraction of medium B with respect to medium A. The index of refraction of water with respect to a vacuum is 1.333. The index of refraction of ice with respect to a vacuum is 1.309. The index of refraction of air with respect to a vacuum is 1.0002.

Figure 5:
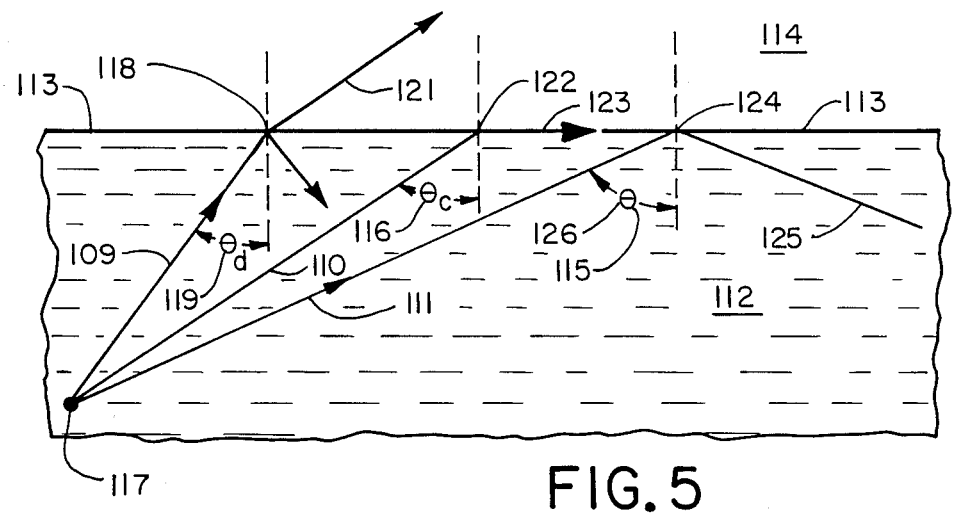
FIG. 5 is a diagrammatic illustration of the internal reflections within a transparent or translucent layer.

The present invention utilizes this difference in refractive index along with absorption characteristics to detect, and therefore, distinguish between the presence of air, water and ice using the principal and techniques of fiber optic refractometry. FIG. 5 illustrates the physical phenomenon called total internal reflection. Total internal reflection is a phenomenon in which electromagnetic radiation 109, 110, 111 in a given medium 112 which is incident on the boundary 113 with a less-dense medium 114 having a lower index of refraction at an angle 115 greater than the critical angle 116 is completely reflected from the boundary interface 113 between the dense medium 112 and less-dense medium 114. To illustrate, ray 109 from point source 117 is incident at 118 on the medium boundary 113. Because angle 119 is less than angle 116, ray 109 is both reflected along ray line 120 and refracted along ray line 121. Ray 110 from point source 117 is incident on the medium boundary 113 at point 122. Because the angle of incidence 116 is equal to the critical angle, the total ray is reflected along ray 123 coincident with the boundary 113. Ray 111 from point source 117 is incident on the medium boundary 113 at point 124. Because the angle of incidence 126 of ray 111 is greater than the critical angle 126, the ray 111 is totally reflected within the dense medium 112 along ray 125.

If we let $n_{112}$ be the refractive index relative to vacuum of the material 112, and if $n_{114}$ is the refractive index relative to vacuum of the material 114, then R1 is the ratio of these indices as follows:

$$R_1 = \frac{n_{112}}{n_{114}}$$

The critical angle 116 and the amount of light transmitted through the interface 113 varies with $R_1$ as described by the Fresnel equations. For an internal reflection ($R_1$ greater than 1) and a constant angle of incidence 119, the amount of light transmitted through the interface 113 along ray 121 increases as $R_1$ decreases. As the amount of light transmitted through interface 113 increases along ray 121, the amount of light reflected internally along ray 120 decreases. For an internal reflection ($R_1$ greater than 1) and a constant angle of incidence 119, the amount of light transmitted through the interface 113 along ray 121 decreases as $R_1$ increases resulting in an increase in the amount of light reflected internally along ray 120. Hence, measurement of the amount of light reflected internally 120 or refracted externally 121 to the dense medium 112 may be used to determine $R_1$. If the index of refraction of either the dense or less dense medium is known, the other may be calculated from the relationship stated previously.

Figure 6:
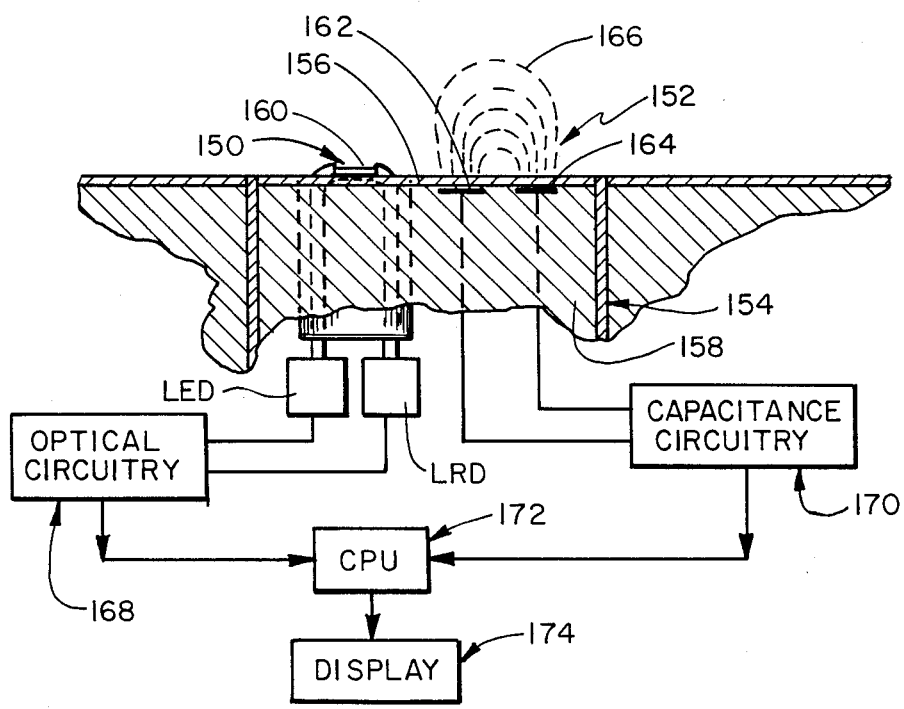
FIG. 6, is a schematic block diagram of a presently preferred embodiment of an ice presence and ice accretion rate sensing system.

FIG. 6 shows a system for detection of the presence of ice and the rate of accretion (buildup) of ice. A bent optical fiber ice presence detection probe means 150, of the type shown in FIGS. 1 & 2, and ice accretion measuring probe means 152 are mounted in juxtaposition to one another in support means 154 including a suitable outer surface 156 covering a body of suitable electrically insulating material 158. The curved portion 160 of the probe means 150 extends above surface 156 for exposure to the environment. Electrodes 162, 164 are located beneath and closely adjacent surface 156 so as to create an electrical field 166 therebetween which extends above surface 156. Thus, the formation of ice on the curved portion 160 of optical fiber probe means 150 provides an ice presence signal from an optometric output means 168 as previously described. The formation of ice on surface 156 above the electrodes 162, 164 interrupts the electrical field 166 and a conventional capacitance measuring circuit means 170 may be used to measure variations in the electrical field. The amount of variation in the electrical field will be proportional to the thickness of the ice on cover surface 156 so that the rate of ice accretion can be determined by correlation between time and thickness in a conventional controller means 172 having a clock circuit and receiving thickness output signals from circuit means 170 as well as ice presence output signals from optometric output means 168. A conventional computer means 174 with a visual display receives output signals from controller means 172 by which ice warning and accretion rate information may be displayed and/or utilized to generate audible and/or visual warning signals. A system of this type is particularly adapted for use at airport runways and vehicle roadways. For such usage, the probe support material 158 and cover surface material 156 preferably correspond to materials used for the runway and/or roadway so as to simulate actual conditions on and in the runway and/or roadway.

An operating principal of the invention comprises the provision of an abraded refracting surface in a fiber optic light path which is located at the in intimate contact with the medium being monitored. Refractive light losses from the refracting surface are related to $R_2$ where $R_2$ is defined $$R_2 = \frac{n_{128}}{n_{133}}$$

where
$n_{128}$ = the refractive index of the fiber optic medium
$n_{133}$ = the refractive index of the test medium The refractive index $n_{128}$ of the fiber optic medium is determined at the time the instrument is designed and constructed, and remains essentially unchanged from the value stated for it by its manufacturer. $R_2$ may be determined for a specific design by calibration using a medium of known index of refraction $n_{133}$. Refractive light losses then from the refracting surface into the test medium and absorption by the test medium are then related to the value of the index of refraction and absorption of medium. Variation in the refractive light losses produces a corresponding variation, as described above, in the light energy transmitted through the fiber optic from the light source to the detection device. Variation in the amount of light transmitted to the light detection device will result in a corresponding direct variation in the output signal from the detection device.

Figure 7:
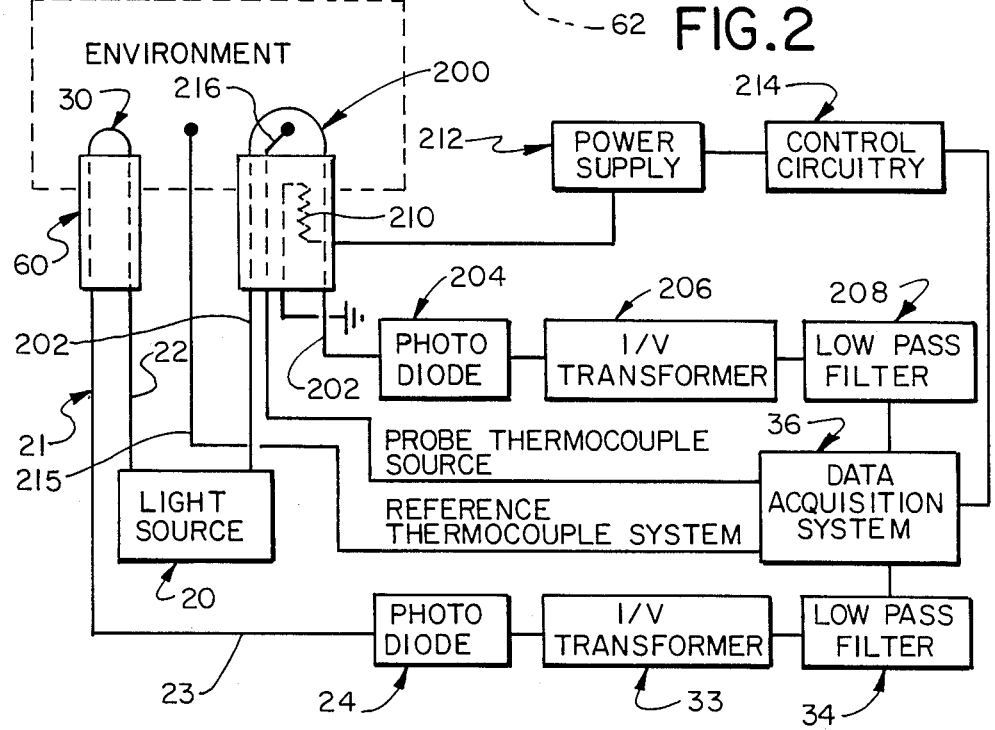
FIG. 7 is a schematic block diagram of an alternative embodiment of an ice presence and ice accretion rate sensing system of the present invention.
Figure 8:
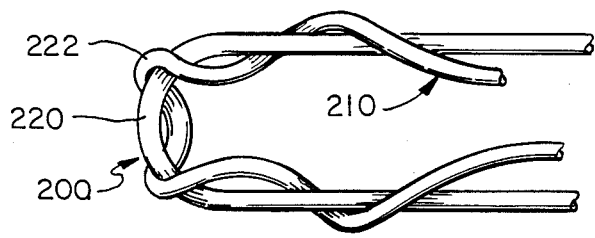
FIG. 8 is a partially broken view of another embodiment of a sensor element according to the present invention.

An alternative embodiment of the invention for the detection of the presence of ice and for obtaining an indication of the thickness of the ice at the site and for determining the rate of accretion or buildup of the ice at the site is shown in FIGS. 7 & 8. Referring to FIG. 7, a first probe 30 is constructed and operates the same as the probe shown in FIGS. 1 & 2. The fiber optic conduit 21 is connected to a light source 20, which may be a conventional laser device, and the intensity of the light from the light source is measured by a photo diode 24 in the same manner as previously described. In this embodiment a second probe 200 of generally similar design is provided which is constructed from a fiber optic conduit 202 which is connected to light source means 20 for receiving light therefrom and to a photo diode detection means 204 and associated transformer circuitry means 206, low pass filter means 208 connected to data acquisition means 36 in the same manner as probe 30. In addition to the foregoing, the probe 200 is provided with a heater means 210 connected to suitable heater circuit means 212 including control circuit means 214 which will energize the heater 210 as soon as any ice is detected on the probe 200 by means of a detected change in the measured light intensity by photo diode 204 and the associated circuitry until the ice is melted and then de-energize the heater until ice again forms on the probe. Thermocouple circuits 215, 216, and a feedback circuit (not shown) are provided to measure the amount of energy being provided to the heater 210 which is a function of the ice accretion rate so that the amount of energy required to repeatedly de-ice the probe 200 and the time required during the period of time that ice is detected on the probe 200 can be used to provide a real time reading of both the ice accretion rate and its thickness. The probe 200 with heater element 210 may be constructed as shown in more detail in FIG. 8 wherein the fiber optic light conduit 220 is wrapped with a resistance heating element 222, such as 0.005 inch diameter Nichrome wire, in the manner shown to optimize the heat transfer to the interface between the probe and the ice at the test site. Icing indication causes the controller to turn on heater 210 which melts the ice formed on the sensing section 200. At indication of water (when the heater melts the ice), the controller shuts the heater off until ice is again sensed. The cycling of the heater is thus repeated during the climatic episode. The controller monitors the power consumed per fixed time interval by the heater. The quantity of power so dissipated is proportional to the ice accretion rate, e.g., the output device could be a watt meter and be calibrated to read inches of ice per minute. The thermocouples 215, 216 allow the controller to have a reference temperature input for calibration purposes. Combining the icing detection device 30 and the icing accretion rate detection device 200 in close proximity allows the detection of the onset, accretion rate and the dissolution of icing at the sensor areas of the instruments.

The system of FIG. 7 detects ice accumulation as a function of the cummulative energy required to remove the ice from the probe tip 200. The operation of this system is as follows: (a) Ice forms on a probe tip and is detected; (b) after a short time delay, an electric current is allowed to pass through resistance element 210 associated with the fiber optic structure; (c) as thermal energy is conducted to the probe tip, ice melts off. The refractometer circuitry 204, 206, 208 detects the change from ice to water. The electric current is interrupted to allow the ice forming cycle to repeat; (d) by signal processing, the electrical energy is summed to yield the power consumed in melting the ice accumulated in the combined time period of initial delay and power application. A combination of factors including energy consumption and time, together with the physical constants related to ice, water and air temperature can be used to calculate ice accumulation per unit of time. The process described in steps (a)–(d) are repeated automatically each time ice is detected as it forms on the probe tip. The total ice accumulation will be the summation of ice accumulation measured during each cycle. The total dissolution of icing is detected by a second reference, non-heated refractometer probe 30 which also indicates the beginning of icing.

The foregoing apparatus and methods provide a system for detection of presence of water and ice and a change of phase of water to ice in the atmosphere by use of fiber optical tube means having an elongated passage therewithin with a first inlet end portion for receiving a beam of light and a second outlet end portion for discharging the beam of light. An intermediate portion of the fiber optical tube means has a specially processed exterior surface providing a light transmission opening means for enabling passage of a portion of the light beam therethrough. Light measuring means are connected to the outlet portion of the fiber optical tube means for measuring the amount of light transmitted thereto and for generating signals indicative of the amount of light received thereby. Mounting means mount the intermediate portion of the fiber optical tube means on a structure having at least one surface exposed to the atmosphere and locate the light transmission opening means in juxtaposition to the surface with the exterior surface of light transmission opening means being located in the atmosphere and being subject to the same atmospheric conditions as the surface. The exterior surface is constructed and arranged to enable accumulation and retention of water thereon for changing the amount of light transmitted through the light transmission opening means and the amount of light transmitted to the light measuring means. A condition indicating means is connected to the light measuring means for indicating the presence of ice on the exterior surface of the light transmission opening means. The exterior surface of the light transmission opening means has a coefficient of friction and surface tension characteristics such as to cause water and ice to adhere thereto. The tubular light transmitting means has an exterior non-translucent covering for defining a substantially closed central cylindrical light path between a light inlet opening and a light outlet opening wherein the amount and intensity of light contained therein is transmitted from the light inlet opening to the light outlet opening without substantial reduction in amount and intensity of light. A selected portion of the exterior covering at a selected portion of the tubular light transmitting means is removed to provide a non-covered section whereat light transmitting surface geometry is substantially different than in the other portions of the tubular light transmitting means. In one embodiment utilizing a U-bend, the selected portion of the tubular light transmitting means is located at an angle of inclination relative to the light inlet opening so as to cause the light to impinge on the selected area at an angle of incidence and reflection whereby a sensed medium material on the non-covered section will cause a detectable difference in the index of refraction and reflection absorption of the light at the non-covered section depending upon the type and condition of the sensed medium material. A mounting means is provided for mounting the light transmitting means in a manner in which the non-covered section is exposed to various having various indices of refraction and reflection causes varying exit conditions of the light beam at the light outlet means. The detector means receive output signals from the light receiving means and generate a control signal indicative of the change in condition on the exterior surface of the selected area of the light transmission means. The exterior detection portion of the light transmitting means has an abraded, non-smooth surface with striations extending transversely to the axis of the light beam and being exposed to the variable external conditions for surface contact by adhesion with and/or immersion in fluids surrounding the exterior portion. In the presently preferred embodiments, the light source means comprises an infrared light emitting device having a wavelength in excess of 600 nanometers. The sensor portion provides between 50 to 70% attenuation losses and causes a signal change shift of at least 30% or more upon change in a condition to be sensed.

The invention has been described by reference to various illustrative embodiments including various forms of apparatus with particular embodiments which may be employed with other embodiments. It is intended that the appended claims be construed to cover various alternative embodiments and modifications except insofar as limited by the prior art.

What is claimed is:

1. A system for detection of a change in and a condition of a selected environment comprising:
    a light source means for continuously generating a beam of light;
    a light receiving and signal generating means for continuously receiving light from said light source means and for generating variable signals dependent upon the amount of light received;
    fiber optic means made of a continuous uninterrupted length of fiber optic material for connecting said light source means to said light receiving and signal generating means and for providing a continuous light path therebetween for continuously transmitting said beam of light from said light source means to said light receiving means along a substantially confined light path;

cover means for said fiber optic means for defining the substantially confined light path;

a sensor portion comprising a peripheral outer surface of said fiber optic means and being uncovered by said cover means and located in the selected environment and being constructed and arranged to cause substantial loss of light in said sensor portion dependent on environmental conditions whereby variable output signals generated by said light receiving and signal generating means vary substantially in accordance with environmental conditions; and condition indicating means connected to said light receiving and signal generating means for indicating changes in environmental conditions.

2. The invention as defined in claim 1, and wherein said sensor portion of said fiber optic means comprises:

an U-shape loop section having a curved portion connecting a pair of straight elongated sections whereby the light beam path changes direction while passing through the U-shape loop portion.

3. The invention as defined in claims 1 or 2 and wherein said outer surface of said sensor portion has striation grooves extending generally laterally relative to the central axis of said fiber optic means.

4. The invention as defined in claim 1 and wherein said light source means comprising an infrared light emitting device having a wavelength in excess of 600 nanometers.

5. The invention as defined in claim 4 and wherein said sensor portion causes a signal change shift of at least 30% or more upon change in a condition to be sensed.

6. The invention as defined in claim 5 and further comprising:

reference signal generating means substantially corresponding to the sensing signal apparatus for generating reference signals.

7. A system for detection of a change of phase of water or ice in an environment comprising:

fiber optical tube means having an elongated passage therein with a first inlet end portion for receiving a beam of light and a second outlet end portion for discharging the beam of light;

an intermediate portion of said fiber optical tube means having an exterior surface providing a light transmission opening means for enabling passage of a portion of the light beam therethrough;

light measuring means connected to said outlet portion of said fiber optical tube means for measuring the amount of light transmitted thereto and for generating signals indicative of the amount of light received thereby;

mounting means for mounting said intermediate portion of said fiber optical tube means on a structure having at least one surface exposed to the surrounding environment and for locating said light transmission opening means in juxtaposition to said one surface with said exterior surface of light transmission opening means being located in the environment and being subject to the same environmental conditions as said one surface;

said exterior surface enabling accumulation and retention of water and ice thereon for changing the amount of light transmitted through said light transmission opening means and the amount of light transmitted to said light measuring means;

condition indicating means connected to said light measuring means for indicating the presence of ice on said exterior surface of said light transmission opening means; and said exterior surface of said intermediate portion of said fiber optical tube means having a non-smooth roughened exterior surface with striations extending transversely to the axis of the light beam.

8. The invention as defined in claim 7 and wherein:

said exterior surface of said light transmission opening means having a coefficient of friction and surface tension characteristics such as to cause water and ice to adhere thereto.

9. The invention as defined in claim 7 and wherein:

said fiber optical tube means having an exterior covering preventing the escape of light from said fiber optical tube means and providing for a beam of light to be normally transmitted therethrough without substantial variation in intensity;

a detection portion of said fiber optical tube means extending at an angle of inclination relative to said inlet portion of said light transmission means; and said detection portion having no exterior covering so that light can be transmitted therethrough subject to refraction substantially the same as the medium in contact with said detection portion.

10. A condition sensing system comprising:

a tubular light transmitting means having an exterior non-translucent covering for defining a substantially closed central cylindrical light path between a light inlet means and a light outlet means wherein the amount and intensity of light contained therein is normally transmitted from the light inlet means to the light outlet means without substantial reduction in amount and intensity of light;

a selected portion of said exterior covering at a selected portion of said tubular light transmitting means being removed to provide a non-covered section whereat the refraction and surface geometry are substantially different than in the other portions of said tubular light transmitting means;

said selected portion of said tubular light transmitting means being constructed and arranged to provide exterior surfaces located at an angle of inclination relative to the path of the light beam so as to cause the light to impinge on said selected area at an angle of incidence and reflection whereby a medium material on said non-covered section will cause a significant detectable difference in absorption and refraction and reflection of the light at said non-covered section dependent upon the type and condition of the medium material;

mounting means for mounting said light transmitting means in a manner in which said non-covered section is exposed to various medium materials having various indices of refraction and reflection and absorption causing varying exit conditions of said light beam at said light outlet means;

light generating means operably associated with said light inlet means for generating a beam of light transmitted through said light transmitting means from said light inlet means to said light outlet means while passing said non-covered section;

light receiving means operably associated with said light outlet means for receiving light from said light generating means through said light transmission means after passing by said non-covered section and for generating output signals indicative of changes in said light beam caused by passage through said light variation means; and detector means for receiving said output signals from said light receiving means and generating a control signal indicative of the change in condition of the medium on said exterior surfaces of said selected area of said light transmission means.

11. The invention as defined in claim 10 and said light transmitting means having a portion wherein the light path is changed at least 90 degrees and wherein there is a translucent light area exposed to the light and wherein the translucent light area has an outer surface subject to contact with variable mediums which produce different refractive indices for the light in said light transmitting means.

12. The invention as defined in claims 1, 7, or 10 and further comprising:
rate of change means for measuring the rate of change of environmental conditions.

13. The invention as defined in claim 12 and wherein said rate of change means comprising:
capacitor sensing means for generating signals indicative of a change in an electrical field depending upon the variable thickness of a medium interrupting the electrical field.

14. The invention as defined in claim 12 wherein said rate of change means comprising:
a pair of sensor devices connected in parallel to control circuit means;
a heating means associated with one of said sensor devices for supplying heat to change the condition at said one of said sensor devices; and
measuring means for measuring the amount of heat required to change the condition to provide an indication of the rate of change of the condition.

15. The invention as defined in claim 14 and further comprising:
a single light source for supplying light to both of said sensor devices.

16. A method of detecting the condition and change in condition of a medium comprising the steps:
connecting a light device to a light responsive device through a fiber optic device having a cylindrical light transmitting core, a coating on the core, and a sheath covering the core and the coating;
removing the coating and the sheath from an intermediate portion of the light transmitting core to expose a portion of the core;
changing the contour of an outer peripheral surface of the exposed portion of the core until between 50% and 70% of light transmitted from the light emitting device to the light responsive device through the fiber optic device is attenuated by losses occurring at the exposed core portion of the core when the exposed core portion is located in a standard environment such as air;
establishing a standard output signal from the light responsive device for the standard environment indicative of contact of the exposed core portion with the standard environment;
establishing a first change of condition output signal from the light responsive device for and indicative of a first non-standard condition by locating the exposed core portion in a first non-standard environment such as water; and
thereafter monitoring the output signals and utilizing the standard output signal and the first non-standard change of condition output signal to provide an indication of change of condition in the environment in which the exposed core portion is located.

17. The method as defined in claim 16 further comprising:
establishing a second change of condition output signal from the light responsive device for and indicative of a second non-standard condition by locating the exposed core portion in a second non-standard environment such as ice; and
thereafter monitoring both the first non-standard and the second non-standard change of condition output signals to provide an indication of both the non-standard environmental condition signals and the change from the first non-standard environmental condition to the second non-standard environmental condition.

18. The method as defined in claims 16 or 17 and further comprising:
providing surface striations extending laterally relative to the central longitudinal axis of the light transmitting core during changing of the contour of the outer peripheral surface of the core.

19. A system for detection of a change in and a condition of a selected environment comprising:
a light source means for continuously generating a beam of light;
a light receiving and signal generating means for continuously receiving light from said light source means and for generating variable signals dependent upon the amount of light received;
fiber optic means for connecting said light source means to said light receiving and signal generating means and for continuously transmitting said beam of light from said light source means to said light receiving means along a substantially confined light path;
cover means for said fiber optic means for defining the substantially confined light path;
a sensor portion of said fiber optic means being uncovered by said cover means and having striation grooves extending generally laterally relative to the central axis of said fiber optic mean and being located in the selected environment and being constructed and arranged to cause substantial loss of light in said sensor portion dependent on environmental conditions whereby variable output signals generated by said light receiving and signal generating means vary substantially in accordance with environmental conditions; and
condition indicating means connected to said light receiving and signal generating means for indicating changes in environmental conditions.

20. The invention as defined in claim 19, and wherein said sensor portion of said fiber optic means comprises:
a U-shape loop section having a curved portion connecting a pair of straight elongated sections whereby the light beam path changes direction while passing through the U-shape loop portion.

21. A system for detection of a change in condition of an environment comprising:
light transmission means for providing an elongated light passage therein between a light source means for continuously generating a beam of light and a light receiving and signal generating means for continuously receiving light from said light source means;

an intermediate portion of said light transmission means having an exterior surface providing a light transmission opening means for enabling passage of a portion of the beam of light therethrough;

said light receiving and signal generating means being connected to said light transmission means for measuring the amount of light transmitted thereto and for generating signals indicative of the amount of light received thereby;

mounting means for mounting said intermediate portion of said light transmission means on a structure having at least one surface exposed to the surrounding environment and for locating said light transmission opening means in juxtaposition to said one surface with said exterior surface of said light transmission opening means being located in the environment and being subject to the same environmental conditions as said one surface;

said exterior surface enabling accumulation and retention of water and ice thereon for changing the amount of light transmitted through said light transmission opening means and the amount of light transmitted to said light receiving and signal generating means;

condition indicating means connected to said light receiving and signal generating means for indicating the presence of ice and water on said exterior surface of said light transmission opening means; and said exterior surface of said intermediate portion having striation grooves extending generally laterally relative to the central axis of said light transmission means.

22. The invention as defined in claim 21 and wherein:
said exterior surface of said light transmission opening means having a coefficient of friction and surface tension characteristics such as to cause water and ice to adhere thereto.

23. The invention as defined in claim 21 and wherein said intermediate portion of said light transmission means comprises:
an U-shape loop section having a curved portion connecting a pair of straight elongated sections whereby the light beam path changes direction while passing through the U-shape loop portion.

24. A system for detection of a change in and a condition of a selected environment comprising:
a light source means for continuously generating a beam of light;
a light receiving and signal generating means for continuously receiving light from said light source means and for generating variable signals dependent upon the amount of light received;
a continuous one-piece light transmission means for connecting said light source means to said light receiving and signal generating means and for continuously transmitting said beam of light from said light source means to said light receiving means along a substantially confined light path;
a sensor portion of said light transmission means being located in the selected environment and being constructed and arranged to cause substantial loss of light in said sensor portion dependent on environmental conditions whereby variable output signals generated by said light receiving and signal generating means vary substantially in accordance with environmental conditions;
condition indicating means connected to said light receiving and signal generating means for indicating changes in environmental conditions; and
wherein said sensor portion has an outer surface with striation grooves extending generally laterally relative to the central axis of said light transmission means.

25. The invention as defined in claim 24, and wherein:
said light transmission means comprises a tubular fiber optic device having an U-shape loop section with a curved portion connecting a pair of straight elongated sections whereby the light beam path changes direction while passing through the U-shape loop portion.

26. A condition sensing system comprising:
a light transmitting means for defining a substantially closed elongated light path between a light inlet means and a light outlet means wherein the amount and intensity of light contained therein is normally transmitted from the light inlet means to the light outlet means without substantial reduction in amount and intensity of light;
a selected intermediate exterior surface portion of said light transmitting mean having striation grooves extending generally laterally relative to the central axis of said light transmitting means whereat the index of refraction and surface geometry are substantially different than in the other portions of said light transmitting means and being constructed and arranged to provide exterior surfaces located at an angle of inclination relative to the path of the light beam so as to cause the light to impinge on said selected area at an angle of incidence and reflection whereby a medium material on said selected intermediate exterior surface portion will cause a significant detectable difference in absorption and refraction and reflection of the light at said selected intermediate exterior surface portion dependent upon the type and condition of the medium material;
mounting means for mounting said light transmitting means in a manner in which said selected intermediate exterior surface portion is exposed to various medium materials having various indices of refraction and reflection and absorption causing varying exit conditions of said light beam at said light outlet means;
light generating means operably associated with said light inlet means for generating a beam of light transmitted through said light transmitting means for said light inlet means to said light outlet means while passing said selected intermediate exterior surface portion;
light receiving means operably associated with said light outlet means for receiving light from said light generating means through said light transmitting means after passing by said selected intermediate exterior surface portion and for generating output signals indicative of changes in said light beam caused by passage through said light variation means; and
detector means for receiving said output signals from said light receiving means and generating a control signal indicative of the change in condition of the medium on said selected intermediate exterior surface portion of said light transmitting means.

27. The invention as defined in claim 26 and wherein:
said selected intermediate exterior surface portion of said light transmitting means having a non-smooth roughened exterior surface with striations extending transversely relative to the axis of the light beam.

28. A method of detecting the condition and change in condition of a medium comprising the steps:
connecting a light emitting device to a light responsive device through a light transmission device having a central light transmitting core and a smooth exterior outer peripheral surface;
changing the contour of the outer peripheral surface of an exposed portion of the core until a substantial amount of the light transmitted from the light emitting device to the light responsive device through the light transmission device is attenuated by losses occurring at the exposed core portion of the core when the exposed core portion is located in a standard environment such as air;
establishing a standard output signal from the light responsive device for the standard environment indicative of contact of the exposed core portion with the standard environment;
establishing a first change of condition output signal from the light responsive device for and indicative of a first non-standard condition by locating the exposed core portion in a first non-standard environment such as water; and
thereafter monitoring the output signals and utilizing the standard output signal and the first non-standard change of condition output signal to provide an indication of change of condition in the environment in which the exposed core portion is located.

29. The method as defined in claim 28 and further comprising:
establishing a second change of condition output signal from the light responsive device for and indicative of a second non-standard condition by locating the exposed core portion in a second non-standard environment such as ice; and
thereafter monitoring both the first non-standard and the second non-standard change of condition output signals to provide an indication of both the non-standard environmental condition signals and the change from the first non-standard environmental condition to the second non-standard environmental condition.

30. The method as defined in claims 28 or 29 and further comprising:
providing outer peripheral surface striations extending laterally relative to the central longitudinal axis of the light transmitting core during changing of the contour of the outer peripheral surface of the core.

* * * * *